United States Patent
Huh

(10) Patent No.: US 10,022,273 B2
(45) Date of Patent: Jul. 17, 2018

(54) FACE PROTECTOR

(71) Applicant: OTOS WING CO., LTD., Seoul (KR)

(72) Inventor: Moon Young Huh, Seoul (KR)

(73) Assignee: OTOS WING CO., LTD., Seoul (KR)

(*) Notice: Subject to any disclaimer, the term of this patent is extended or adjusted under 35 U.S.C. 154(b) by 3 days.

(21) Appl. No.: 15/388,390

(22) Filed: Dec. 22, 2016

(65) Prior Publication Data

US 2018/0161208 A1    Jun. 14, 2018

(30) Foreign Application Priority Data

Dec. 8, 2016 (KR) .......................... 10-2016-0166822

(51) Int. Cl.
*A61F 9/06* (2006.01)
*A61F 9/02* (2006.01)

(52) U.S. Cl.
CPC ................ *A61F 9/06* (2013.01); *A61F 9/025* (2013.01)

(58) Field of Classification Search
CPC .. A61F 9/06; A61F 9/061; A61F 9/062; A61F 9/064
USPC ...................................... 2/8.2–8.5
See application file for complete search history.

(56) References Cited

U.S. PATENT DOCUMENTS

| | | | | |
|---|---|---|---|---|
| 3,214,767 A * | 11/1965 | Weber | ....... | A61F 9/06 2/9 |
| 5,029,342 A * | 7/1991 | Stein | ....... | A61F 9/068 136/291 |
| 5,673,431 A * | 10/1997 | Batty | ....... | A42B 3/225 2/10 |
| 6,591,424 B1 * | 7/2003 | Wang-Lee | ....... | A61F 9/064 2/424 |
| 7,000,251 B2 * | 2/2006 | DeYoung | ....... | A61F 9/06 2/11 |
| 2004/0179149 A1 * | 9/2004 | Wang-Lee | ....... | A61F 9/061 349/58 |
| 2012/0031413 A1 * | 2/2012 | Shi | ....... | A41D 13/11 128/858 |

* cited by examiner

*Primary Examiner* — Timothy K Trieu
(74) *Attorney, Agent, or Firm* — Cantor Colburn LLP

(57) ABSTRACT

Provided is a face protector provided with a transparent film sheet to protect a viewing window of any one working mask selected from a safety face shield or a welding helmet. One or more transparent film sheets are inserted into a gap between the surface of the upper part of the viewing window and the bent inner surface of an upper support brim and thus combined with the surface of the viewing window, thereby preventing contaminants, paints, slag or metal particles, which may contaminate the viewing window during a working process, from being attached to the viewing window, securing a worker's clear view to increase worker safety, and to greatly extending the working mask.

6 Claims, 13 Drawing Sheets

FACE PROTECTOR

BACKGROUND OF THE INVENTION

Field of the Invention

The present invention relates to a working mask of a safety face shield or a welding helmet, with which a transparent film sheet to protect a viewing window is combined, and more particularly to a face protector, in which a transparent film sheet is inserted into a gap between the surface of a viewing window and the bent inner surface of an upper support brim and thus combined with the surface of the viewing window, so as to prevent welding flame contaminants, paints, slag or metal particles, which may contaminate the viewing window during a working process, from being attached to the viewing window, and to prevent scratches occurring on the viewing window of a safety face shield, a welding helmet or goggles from disturbing a worker's field of vision.

Description of the Related Art

A conventional working mask includes a safety helmet, a mask cover and a viewing window.

In the conventional working mask, the safety helmet is mounted within the mask cover, and a worker wearing the working mask executes work through the viewing window.

In general, in case of general painting, spraying of agricultural chemicals, painting of the bottom surface of a ship, dust work, protection against dust, sanding, grinding, coal mining and tunnel excavation under poor working surroundings, paints, adhesive foreign substances, adhesive dust or adhesive particles are attached to the viewing window of the conventional working mask and remain despite cleaning or washing of the viewing window after these operations. Therefore, as the number of usage of the working mask increases, the surface of the viewing window is scratched and obstructs a worker's field of vision so that it is difficult for the worker to judge objects and, thus, the viewing window needs to be discarded or replaced.

Further, if the viewing window is damaged, the viewing window should be replaced or the working mask may be damaged. Further, in the conventional working mask, slag or metal particles scattered during general painting, welding, grinding, painting of the bottom surface of a ship, dust work, protection against dust, sanding, coal mining or tunnel excavation, may collide with the viewing window and thus scratch or contaminate the viewing window.

Further, in order to prevent slag or metal particles scattered during general painting, welding, grinding, painting of the bottom surface of a ship, dust work, protection against dust, sanding, coal mining or tunnel excavation from being scattering and thus colliding with a transparent viewing window of a conventional working mask, a safety face shield, or goggles, a protective unit provided in front of the transparent viewing window is fitted into the transparent viewing window to protect the transparent viewing window but paints, slag or metal particles are attached to the transparent viewing window and thus the transparent viewing window is contaminated or needs to be replaced, thus causing cumbersomeness.

SUMMARY OF THE INVENTION

Therefore, the present invention has been made in view of the above problems, and it is an object of the present invention to provide a face protector, in which a transparent film sheet to protect a viewing window is inserted into a gap between the surface of the viewing window and the bent inner surface of an upper support brim and thus combined with the surface of the viewing window, so as to protect the viewing window from welding flame contaminants, paints, slag or metal particles, which may contaminate the viewing window during a working process, to prevent scratches occurring on the viewing window of a safety face shield or a welding helmet from disturbing a worker's field of vision, and to greatly extend the lifespan of the working mask.

It is another object of the present invention to provide a face protector, in which a transparent film sheet is combined with the surface of a viewing window through a sliding method and fixation of the transparent film sheet to the viewing window is carried out using protrusions formed integrally with an upper support brim.

It is yet another object of the present invention to provide a face protector, in which one or more transparent film sheets are stacked and attached to the surface of a viewing window so that the transparent film sheets may be removed one by one so as to prevent disturbance to a worker's field of vision when the viewing window is contaminated and, thus, a clear view may be secured without stoppage of work and work may be smoothly carried out.

In accordance with an aspect of the present invention, the above and other objects can be accomplished by the provision of a face protector provided with a transparent film sheet to protect a viewing window of any one working mask selected from a safety face shield or a welding helmet, wherein the working mask is configured such that the transparent film sheet is inserted into a gap between the surface of the viewing window and a bent inner surface of an upper support brim, formed above the viewing window, through a sliding method so as to be combined with the surface of the viewing window, the transparent sheet is formed of any one selected from the group consisting of PET, PP and PC, and includes a plurality of fixing holes, and the upper support brim includes a plurality of fixing protrusions formed below a fixing rib on the bent inner surface of the upper support brim, and the transparent film sheet is fixed to the surface of the viewing window by inserting the fixing protrusions of the upper support brim into the fixing holes of the transparent film sheet.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
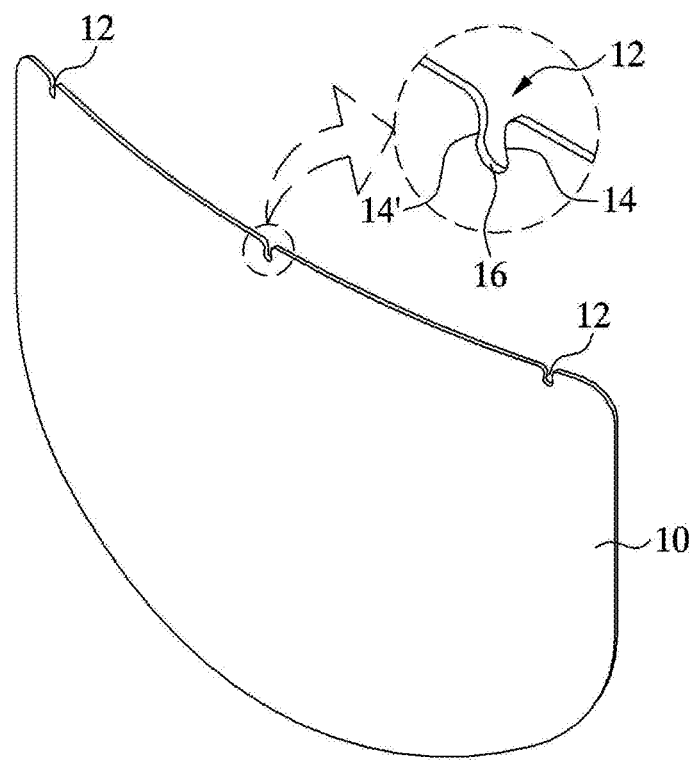
FIG. 1 is a perspective view illustrating a transparent film sheet of a face protector, with which the transparent film sheet to protect a viewing window is combined, in accordance with one embodiment of the present invention.

Now, preferred embodiments in accordance with the present invention will be described in detail with reference to the annexed drawings.

Terms used in the following description or the claims are not interpreted as having conventional or dictionary meanings and, in order to describe the invention in the best mode by the inventor(s), the definitions of these terms should be determined based on the whole content of this specification.

Therefore, the embodiments stated in the specification and elements illustrated in the drawings have been made only for a better understanding of the present invention and those skilled in the art will appreciate that various modifications, additions, and substitutions to the specific elements are possible, without departing from the scope and spirit of the invention as disclosed in the accompanying claims.

The present invention relates to a face protector provided with a transparent film sheet 10 to protect a viewing window 100 of any one working mask selected from a safety face shield or a welding helmet, wherein the working mask is configured such that the transparent film sheet 10 is inserted into a gap between the surface of the viewing window 100 and a bent inner surface of an upper support brim 120 through a sliding method so as to be combined with the surface of the viewing window 100, the transparent sheet 10 is formed of any one selected from the group consisting of PET, PP and PC and includes a plurality of fixing holes 12 formed at the upper end thereof, the upper support brim 120 includes a plurality of fixing protrusions 20 formed below a fixing rib 130 on the bent inner surface of the upper support brim 120, and the transparent film sheet 10 is fixed to the surface of the viewing window 100 by inserting the fixing protrusions 20 of the upper support brim 120 into the fixing holes 12 of the transparent film sheet 10.

The fixing hole 12 includes fixing projections 14 and 14' formed at both ends of an entrance of the fixing hole 12, and an inner recess 16 formed between the fixing projections 14 and 14'.

The fixing holes 12 of the transparent film sheet 10 are formed as through holes formed through the transparent film sheet 10.

Figure 2:
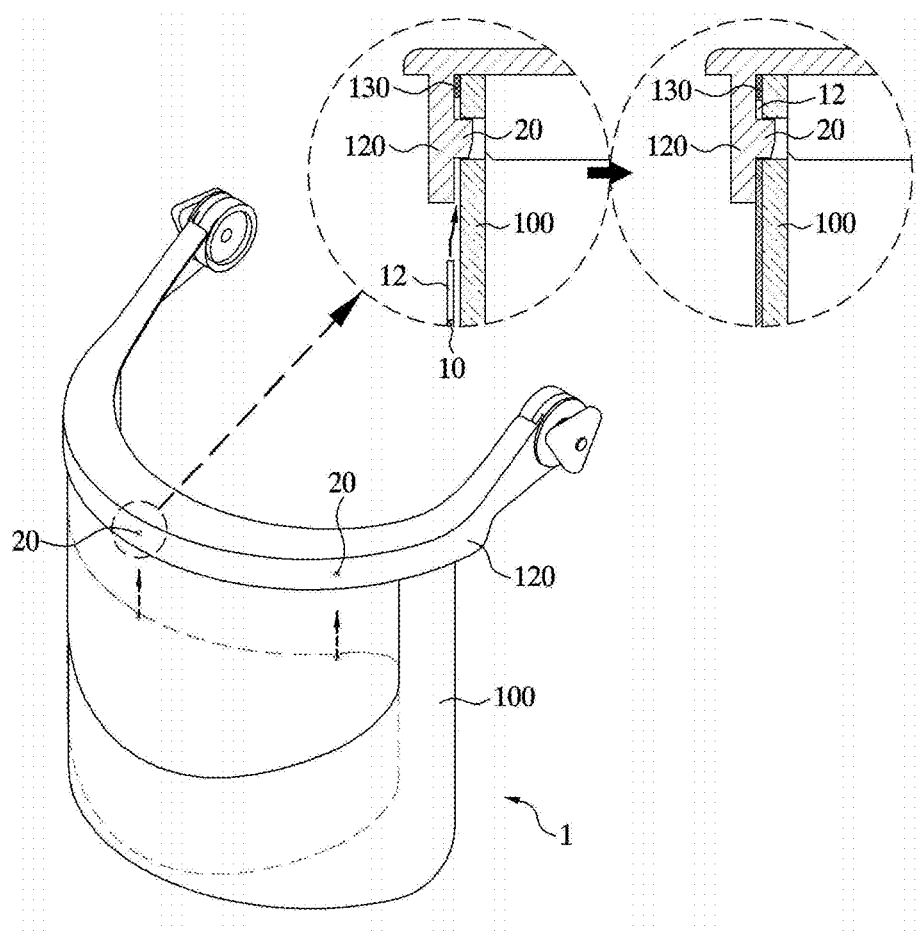
FIG. 2 is a perspective view illustrating a use state of a transparent film sheet in accordance with the present invention, applied to a safety face shield.

As exemplarily shown in FIGS. 1 and 2, in a working mask of a safety face shield in accordance with one embodiment of the present invention, a viewing window 100 is combined with the lower portion of an upper support brim 120, and a transparent film sheet 10 is inserted into a gap between the surface of the viewing window 100 and the bent inner surface of the upper support brim 120, so as to be combined with the surface of the viewing window 100, and may thus be used as a disposable consumable and prevent paints, slag or metal particles, which may contaminate the viewing window 100 during a working process, from being attached to the viewing window 100. Further, the transparent film sheet 10 may not only protect the viewing window 100 of the safety face shield or a welding helmet from scratches so as to prevent disturbance to a worker's field of vision but also greatly extend the lifespan of the working mask.

In the present invention, the transparent film sheet 10 protects a worker's face from various scattered objects and harmful fragments, which may be generated during scattered dust work or welding operation. In the present invention, the transparent film sheet 10 is formed of polyethylene terephthalate (PET), polypropylene (PP) or polycarbonate (PC) and thus has excellent heat resistance, chemical resistance and durability. In the present invention, the transparent film sheet 10 has a thickness of 0.1 to 0.3 mm and is thus light and transparent.

In the present invention, when the transparent film sheet 10 is combined with the viewing window 100, the transparent film sheet 10 may be fixed to the viewing window 100 without any fastening part, and a plurality of transparent film sheets 10 may be repeatedly stacked and thus manufacturing costs may be reduced.

As exemplarily shown in FIGS. 1 and 2, in the working mask of this embodiment of the present invention, a plurality of fixing holes 12 is formed at the upper end of the transparent film sheet 10, a plurality of fixing protrusions 20 is formed on the bent inner surface of the upper support brim 120, the transparent film 10 is fixed to the surface of the viewing window 100 by inserting the fixing protrusions 20 of the upper support brim 120 into the fixing holes 12 of the transparent film sheet 10, and, thus, the transparent film sheet 10 may be used as a disposable consumable.

As exemplarily shown in FIGS. 1 and 2, fixing projections 14 and 14' are formed at both ends of an entrance of the fixing hole 12 of the working mask of this embodiment of the present invention and an inner recess 16 is formed between the fixing projections 14 and 14', and, thus, the transparent film 10 is fixed to the surface of the viewing window 100 by inserting the fixing protrusions 20 of the upper support brim 120 into the fixing holes 12 of the transparent film sheet 10 so as to be used as a disposable consumable.

In the present invention, when the transparent film sheet 10 is combined with the surface of the viewing window 100, the transparent film sheet 10 is fastened to the surface of the viewing window 100 through a sliding method. In order to fix the transparent film sheet 10, the fixing protrusions 20 are formed integrally with the upper support brim 120.

Figure 3:
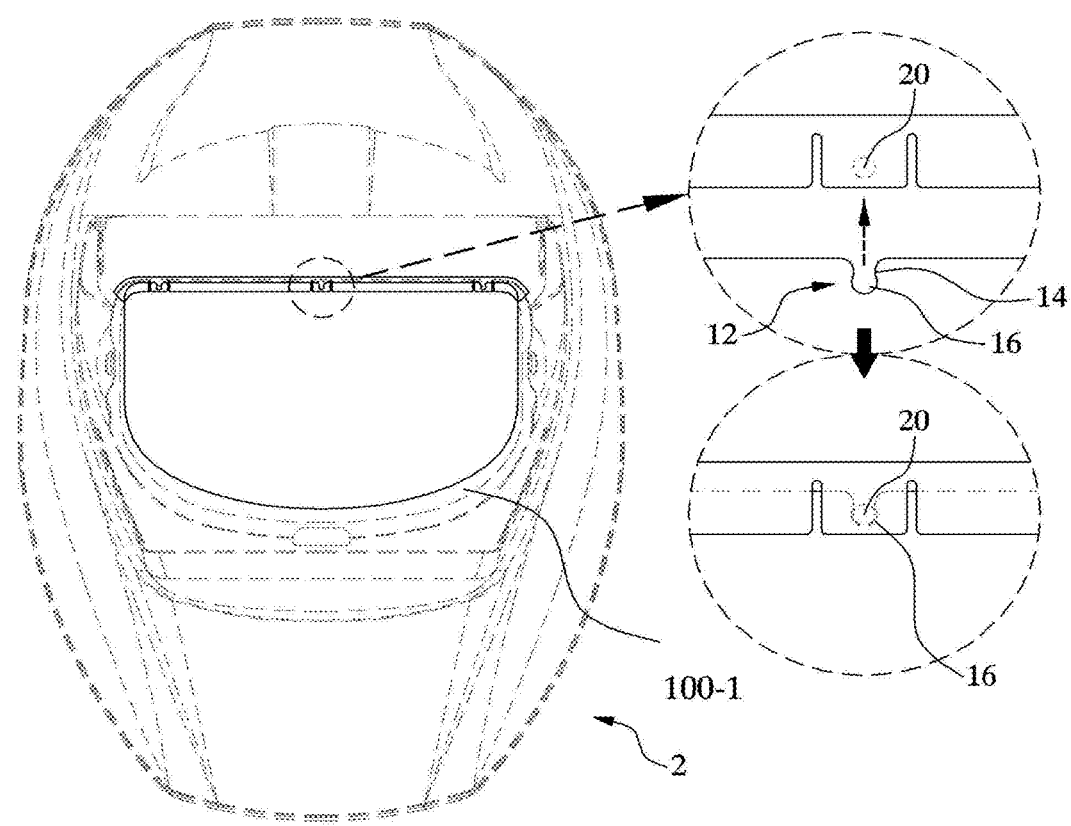
FIG. 3 is a perspective view illustrating a use state of a transparent film sheet in accordance with the present invention, applied to a welding helmet.
Figure 4:
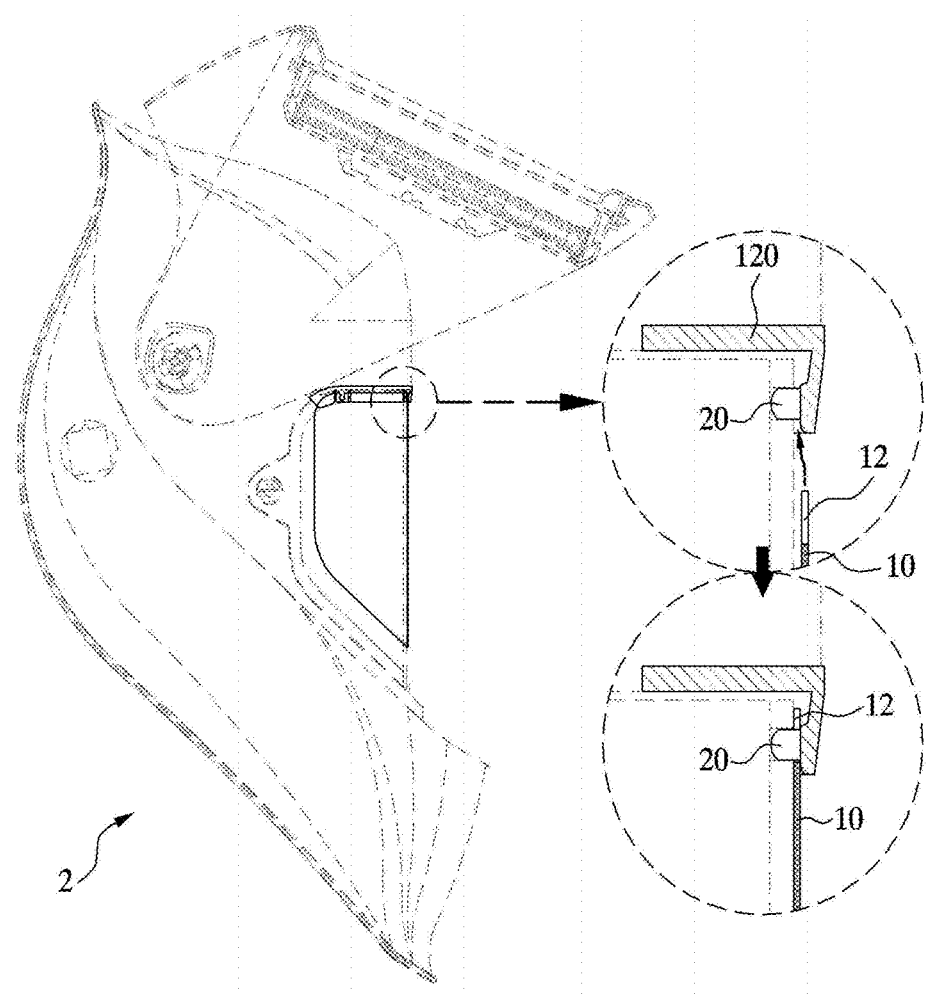
FIG. 4 is a cross-sectional view of the transparent film sheet in accordance with the present invention, mounted on the welding helmet.

As exemplarily shown in FIGS. 1, 3 and 4, in a working mask of a welding helmet in accordance with another embodiment of the present invention, a viewing window 100-1 is combined with the lower portion of an upper support brim 120, and a transparent film sheet 10 is inserted into a gap between the surface of the viewing window 100-1 and a bent inner surface of the upper support brim 120, so as to be combined with the surface of the viewing window 100-1, and may thus prevent dust contaminants, welding flame contaminants, paints, slag or metal particles, which may contaminate the viewing window 100-1 during a working process, from being attached to the viewing window 100-1 and greatly extend the lifespan of the working mask as well as the viewing window.

As exemplarily shown in FIGS. 1, 3 and 4, in the working mask of the welding helmet in accordance with this embodiment of the present invention, a plurality of fixing holes 12 is formed at the upper end of the transparent film sheet 10 and a plurality of fixing protrusions 20 is formed on the bent inner surface of the upper support brim 120, and the transparent film 10 is fixed to the surface of the viewing window 100-1 by inserting the fixing protrusions 20 of the upper support brim 120 into the fixing holes 12 of the transparent film sheet 10.

As exemplarily shown in FIGS. 1, 3 and 4, fixing projections 14 and 14' are formed at both ends of an entrance of the fixing hole 12 of the working mask of the welding helmet of this embodiment and an inner recess 16 is formed between the fixing projections 14 and 14', and, thus, the transparent film 10 is fixed to the surface of the viewing window 100-1 by inserting the fixing protrusions 20 of the upper support brim 120 into the fixing holes 12 of the transparent film sheet 10.

Further, when the transparent film sheet 10 is combined with the upper part of the viewing window 20 to fix the transparent film sheet 10, the fixing holes 12 formed on the transparent film sheet 10 are fitted into one selected from the upper surface, the upper, left and right surfaces, and the upper, lower, left and right surfaces of a frame fixing the viewing window 100.

Figure 5:
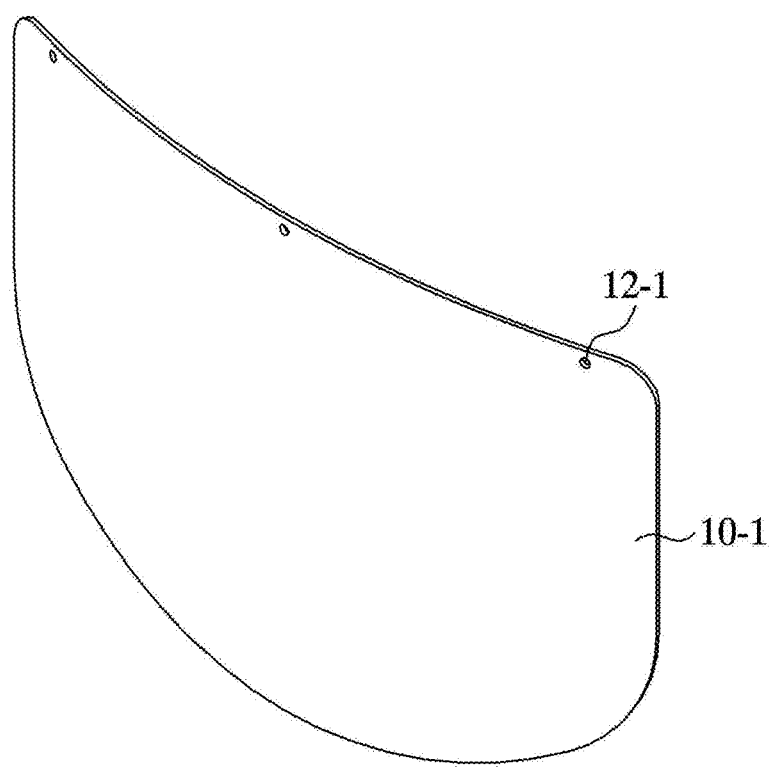
FIG. 5 is a perspective view illustrating a transparent film sheet of a face protector, with which the transparent film sheet to protect a viewing window is combined, in accordance with a further embodiment of the present invention.
Figure 6:
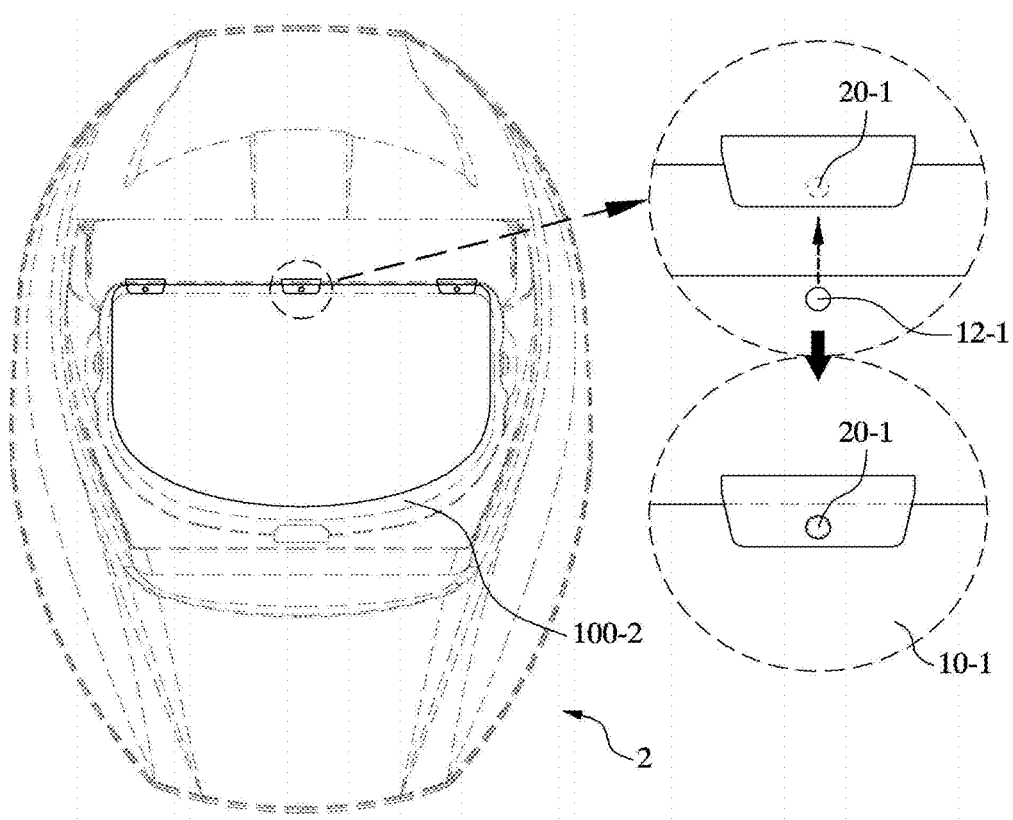
FIG. 6 is a perspective view of a welding helmet, with which a transparent film sheet in accordance with the present invention is combined.
Figure 7:
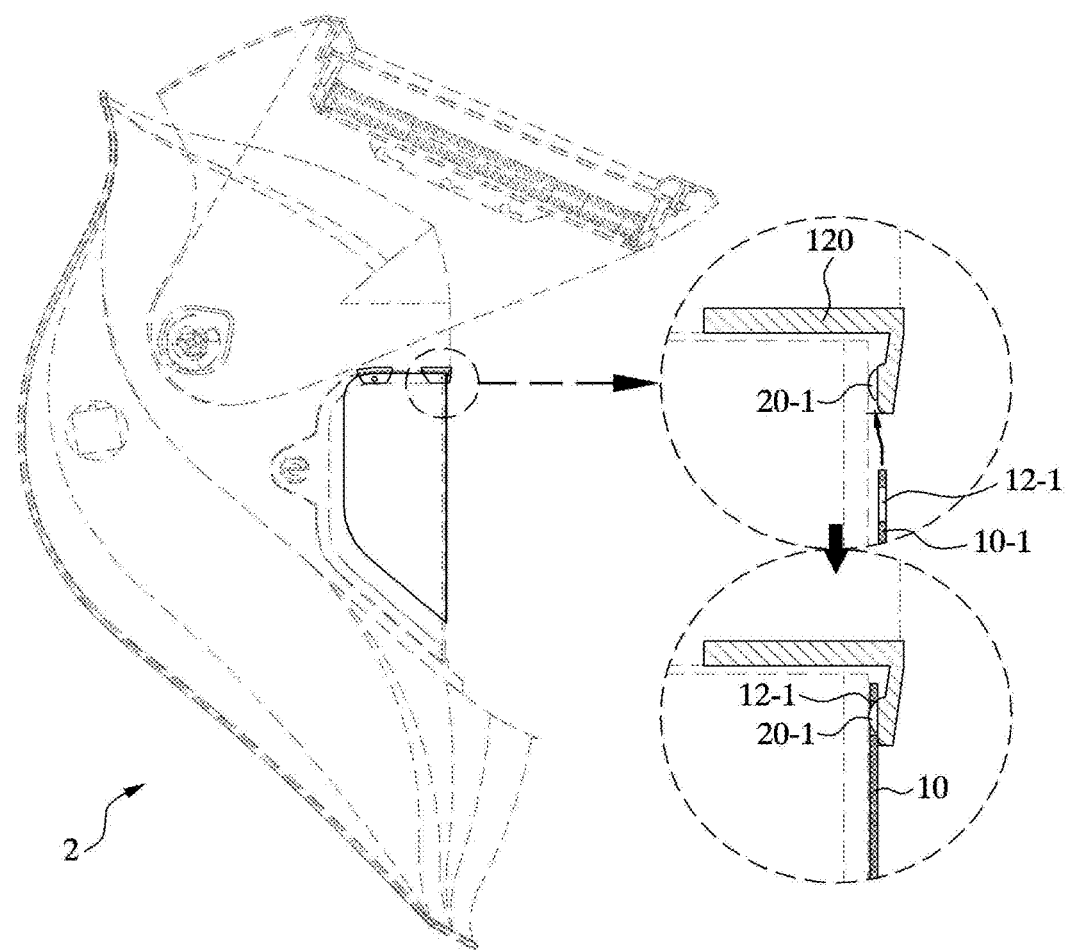
FIG. 7 is a cross-sectional view of the welding helmet, with which the transparent film sheet in accordance with the present invention is combined.

As exemplarily shown in FIGS. 5, 6 and 7, in a working mask in accordance with a further embodiment of the present invention, fixing holes 12-1 are formed on a transparent film sheet 10-1 as through holes, and the transparent film sheet 10-1 is fixed to the surface of a viewing window 100-2 by inserting fixing protrusions 20-1 of an upper support brim 120-1 into the fixing holes 12-1 of the transparent film sheet 10-2.

Figure 8:
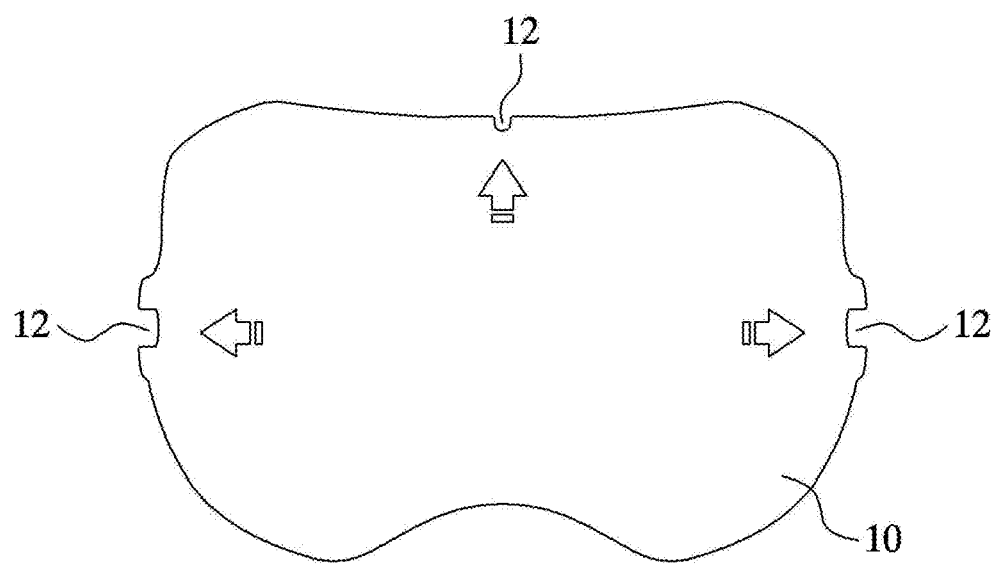
FIGS. 8 to 10 are views illustrating the structures of transparent film sheets in accordance with other embodiments of the present invention and a use state of the transparent film sheet mounted on a welding helmet.

As exemplarily shown in FIG. 8, in a face protector, with which a transparent film sheet 10 to protect a viewing window is combined, in accordance with another embodiment of the present invention, the transparent film sheet 10 is fixed to the surface of the viewing window by inserting fixing protrusions formed on an upper support brim 120 and left and right frames into fixing holes 12 formed at the upper end and the left and right ends of the transparent film sheet 10.

Figure 9:
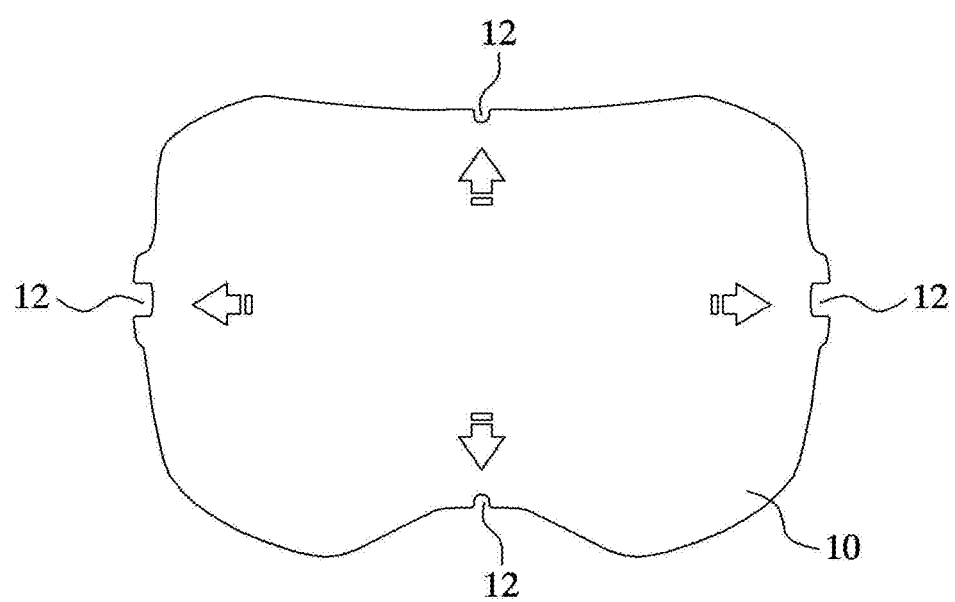
Figure 10:
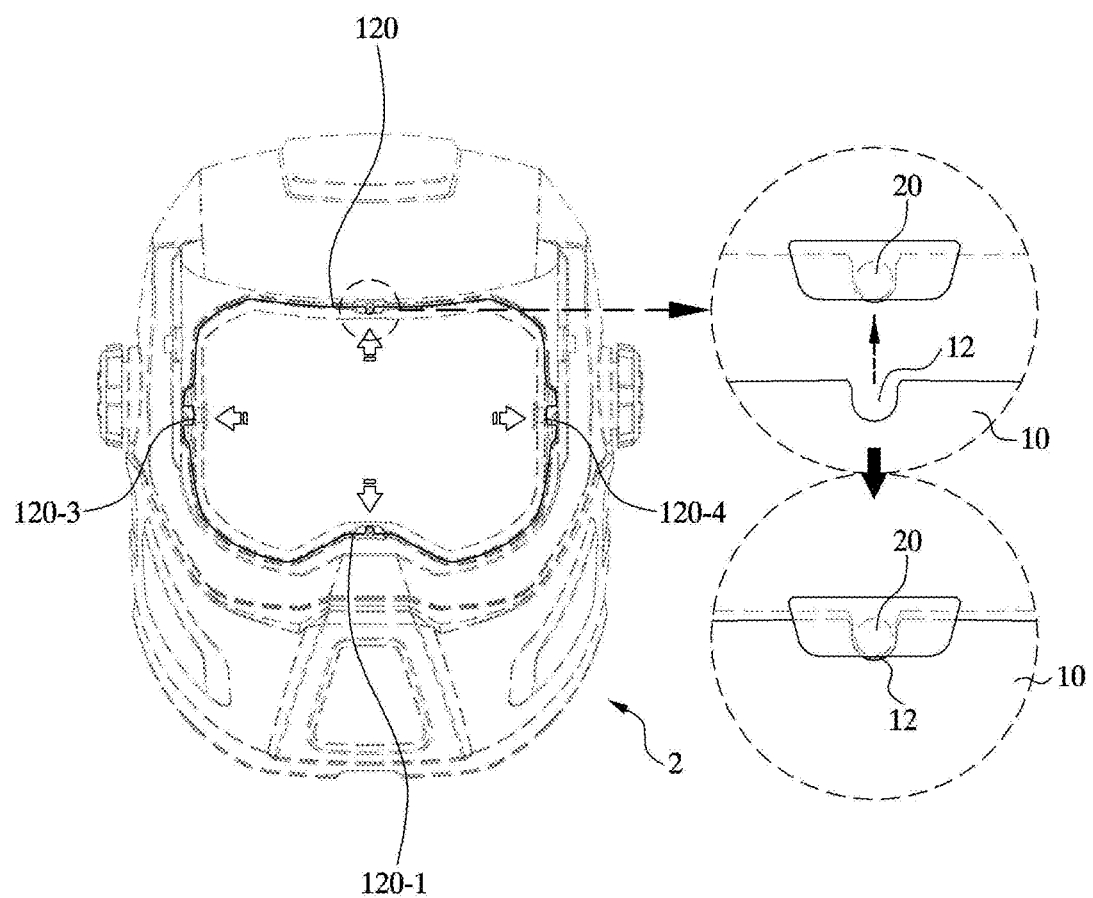

FIGS. 9 and 10 illustrate a face protector applied to a welding helmet in accordance with another embodiment of the present invention. In the face protector, with which a transparent film sheet 10 to protect a viewing window 100 is combined, in accordance with this embodiment, the transparent film sheet 10 is fixed to the surface of the viewing window by inserting fixing protrusions 20 of upper and lower support brims 120 and 120-1 and left and right frames 120-3 and 120-4 into fixing holes 12 formed at the upper, lower, left and right ends of the transparent film sheet 10.

Figure 11:
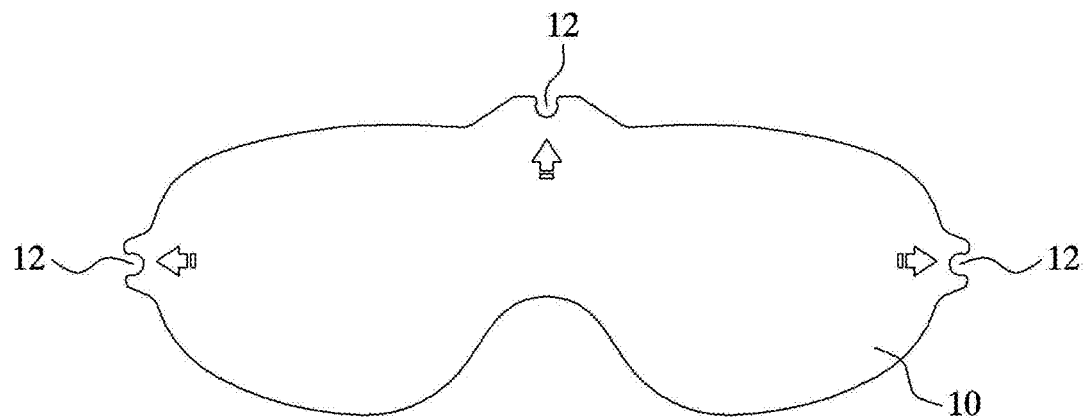
FIGS. 11 to 13 are views illustrating the structures of transparent film sheets in accordance with other embodiments of the present invention and a use state of the transparent film sheet mounted on goggles.
Figure 12:
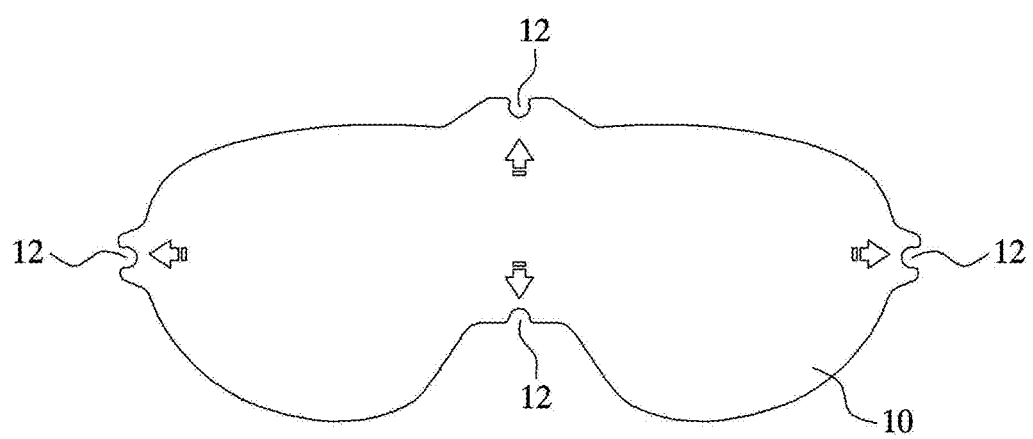

FIGS. 11 and 12 illustrate transparent film sheets 10 in accordance with other embodiments of the present invention applied to goggles 3. In a face protector, with which the transparent film sheet 10 to protect a viewing window is combined, in accordance with these embodiment, the transparent film sheet 10 is fixed to the surface of the viewing window by inserting fixing protrusions 20 formed at an upper support brim 120 and the left and right surfaces of a frame of the goggles 3 into fixing holes 12 formed at the upper, left and right ends of the transparent film sheet 10 or by inserting fixing protrusions 20 formed at the upper support brim 120 and the lower, left and right surfaces of the frame of the goggles 3 into fixing holes 12 formed at the upper, lower, left and right ends of the transparent film sheet 10.

Figure 13:
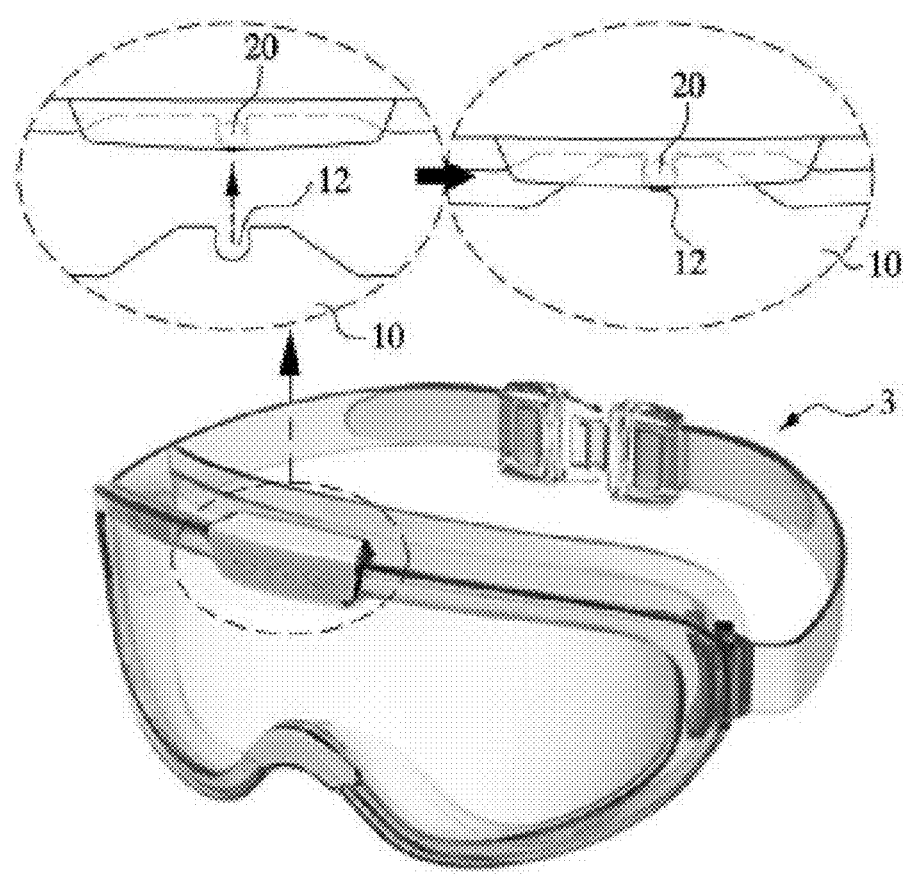

FIGS. 11 to 13 are views illustrating the structures of the transparent film sheets in accordance with these embodiments of the present invention and a use state of the transparent film sheet mounted on the goggles 3. The transparent film sheets 10 in accordance with these embodiments are configured so as to solve washing or replacement of a lens (a viewing window) of the goggles 3 if it is difficult for the worker wearing the goggles 3 to work due to foreign substances blocking the lens of the goggles 3. When the transparent film sheet 10 is combined with the upper part of the viewing window to fix the transparent film sheet 10, the fixing holes 12 of the transparent film sheet 10 are fitted into one selected from the upper surface, the upper, left and right surfaces, and the upper, lower, left and right surfaces of a frame fixing the viewing window.

As described above, the fixing holes 12 of the transparent film sheet 10 are formed on one selected from the upper surface, the upper, left and right surfaces, and the upper, lower, left and right surfaces of the transparent film sheet 10.

Figure 14:
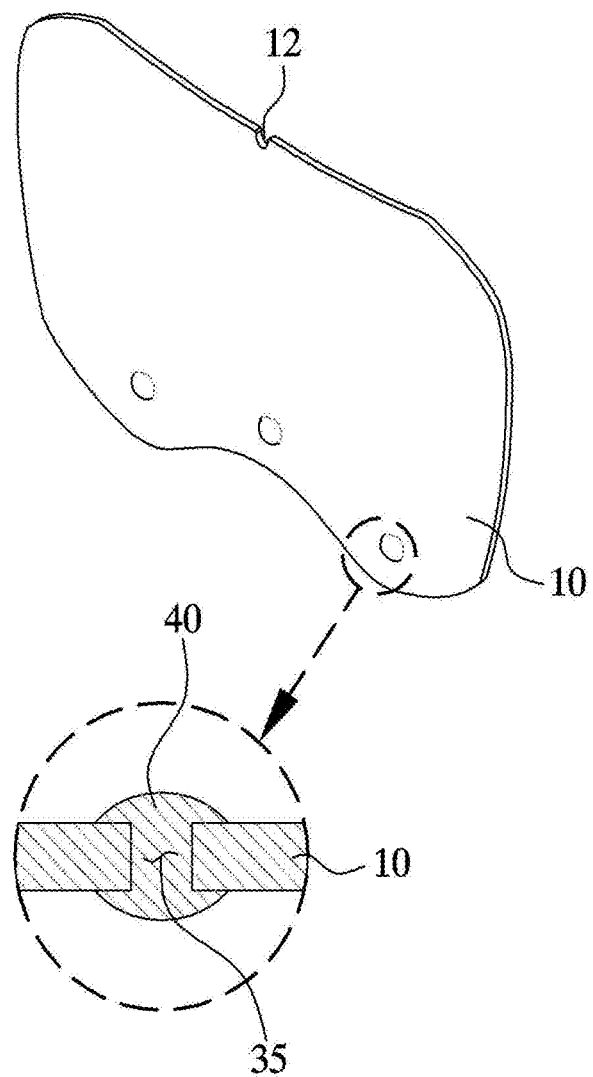
FIGS. 14 and 15 are perspective views illustrating transparent film sheets in accordance with other embodiments of the present invention.

In a face protector, with which a transparent film sheet 10 to protect a viewing window is combined, in accordance with another embodiment of the present invention, as exemplarily shown in FIG. 14, mounting holes 35 are formed through the transparent film sheet 10 and then rubber balls 40 are inserted into the mounting holes 35 so as to prevent the transparent film sheet 10 from being separated from the viewing window.

Figure 15:
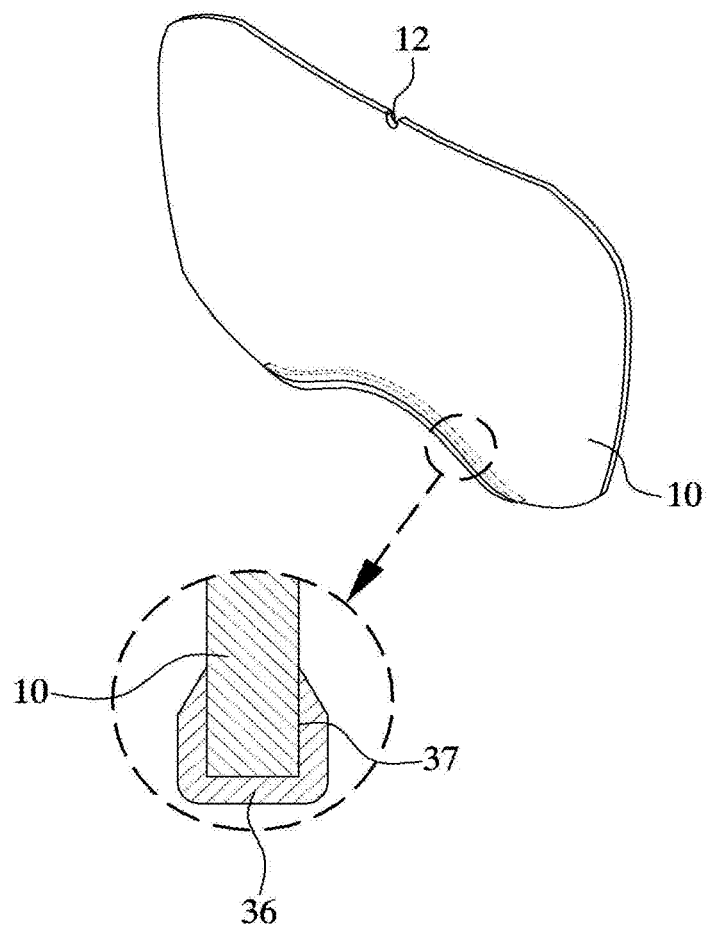

Further, in a face protector, with which a transparent film sheet 10 to protect a viewing window is combined, in accordance with another embodiment of the present invention, as exemplarily shown in FIG. 15, a molding part 36 provided with an insertion groove 37 is fastened to the edge of the lower end of the transparent film sheet 10 such that the molding part 36 may be seen, thereby allowing the transparent film sheet 10 to be conveniently attached to and detached from the viewing window. The molding part 36 may be formed of rubber and have various colors.

As apparent from the above description, in a face protector, with which a transparent film sheet to protect a viewing window is combined, in accordance with the present invention, the viewing window is combined with the lower portion of an upper support brim, and the transparent film sheet is inserted into a gap between the surface of the viewing window and the bent inner surface of the upper support brim so as to be combined with the surface of the viewing window, thereby preventing welding flame contaminants, paints, slag or metal particles, which may contaminate the viewing window during a working process, from being attached to the viewing window, preventing disturbance to a worker's field of vision due to occurrence of scratches on the viewing window of a safety face shield or a welding helmet, and greatly extending the lifespan of the face protector.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A face protector provided with a transparent film sheet to protect a viewing window of any one working mask selected from a safety face shield or a welding helmet, wherein: the transparent film sheet is in a gap between an outer surface of the viewing window and a bent inner surface of an upper support brim, formed above the viewing window, and combine with the outer surface of the viewing window;

the transparent sheet is formed of any one selected from the group consisting of polyethylene terephthalate, polypropylene and polycarbonate, and includes a plurality of fixing holes; and the upper support brim includes a plurality of fixing protrusions formed below a fixing rib on the bent inner surface of the upper support brim, and the transparent film sheet is fixed to the outer surface of the viewing window by inserting the fixing protrusions of the upper support brim into the plurality of fixing holes of the transparent film sheet; wherein the fixing hole includes fixing projections formed at both ends of an entrance of the fixing hole, and an inner recess formed between the fixing projections to receive said protrusion; furthermore comprising a plurality of the transparent film sheets are stacked and fixed to the viewing window configured to be removed one by one.

2. The face protector according to claim 1, wherein the transparent film sheet is fastened to the outer surface of the viewing window, and the fixing protrusions are formed integrally with the upper support brim.

3. The face protector according to claim 1, wherein each of the fixing holes of the transparent film sheet formed by through hole that extending through a thickness of the transparent film sheet.

4. The face protector according to claim 1, wherein the viewing window is one selected from a viewing window of the safety face shield, a viewing window of the welding helmet and a viewing window of goggles.

5. The face protector according to claim 1, wherein the transparent film sheet has a thickness of 0.1 to 0.3 mm.

6. The face protector according to claim 1, wherein, when the transparent film sheet is combined with an upper part of the viewing window to fix the transparent film sheet, the fixing holes of the transparent film sheet are fitted into one selected from an upper surface, the upper part and left and right surfaces of the viewing window.

* * * * *